(12) United States Patent
Doschak et al.

(10) Patent No.: US 9,718,868 B2
(45) Date of Patent: Aug. 1, 2017

(54) PARATHYROID HORMONE, INSULIN, AND RELATED PEPTIDES CONJUGATED TO BONE TARGETING MOIETIES AND METHODS AND MAKING AND USING THEREOF

(71) Applicant: THE GOVERNORS OF THE UNIVERSITY OF ALBERTA, Edmonton (CA)

(72) Inventors: Michael Doschak, Edmonton (CA); Yang Yang, Edmonton (CA); Krishna Hari Bhandari, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 14/424,493

(22) PCT Filed: Aug. 28, 2013

(86) PCT No.: PCT/IB2013/002349
§ 371 (c)(1),
(2) Date: Feb. 27, 2015

(87) PCT Pub. No.: WO2014/033540
PCT Pub. Date: Mar. 6, 2014

(65) Prior Publication Data
US 2015/0246957 A1 Sep. 3, 2015

Related U.S. Application Data

(60) Provisional application No. 61/693,818, filed on Aug. 28, 2012.

(51) Int. Cl.
| | | |
|---|---|---|
| *A61K 47/48* | (2006.01) | |
| *A61K 38/29* | (2006.01) | |
| *A61K 31/663* | (2006.01) | |
| *C07K 14/635* | (2006.01) | |
| *A61P 19/02* | (2006.01) | |
| *C07K 14/62* | (2006.01) | |
| *C07K 14/65* | (2006.01) | |
| *C08F 299/02* | (2006.01) | |

(52) U.S. Cl.
CPC ............ *C07K 14/62* (2013.01); *A61K 31/663* (2013.01); *A61K 38/29* (2013.01); *A61K 47/48084* (2013.01); *A61K 47/48215* (2013.01); *C07K 14/635* (2013.01); *C07K 14/65* (2013.01); *C08F 299/02* (2013.01)

(58) Field of Classification Search
None
See application file for complete search history.

(56) References Cited

U.S. PATENT DOCUMENTS

2006/0153839 A1* 7/2006 Mohamed .......... C07K 16/1278
424/143.1
2007/0134245 A1* 6/2007 Kostenuik .......... A01K 67/0278
424/145.1

FOREIGN PATENT DOCUMENTS

WO 2011045668 4/2011

OTHER PUBLICATIONS

Hammonds et al., J. Biol. Chem., 1989, vol. 264(25):14806-14811.*
Uludag et al., Biotechnol. Prog., 2000, vol. 16(2):258-267.*
Partial Supplementary European Search Report for application 13832369.6-1402/2890708 dated Feb. 5, 2016.
Low et al., "Targeting polymer therapeutics to bone," Adv. Drug. Delivery. Rev. (2012), 64:1189-1204.
Gittens et al., "Designing proteins for bone targeting," Adv. Drug. Delivery Rev. (2005), 57:1011-1036.
Ponnapakkam et al. "A single injection of the anabolic bone agent, parathyroid hormone-collagen binding domain (PTH-CBD), results in sustained increases in bone mineral density for up to 12 months in normal female mice," 2012, Calcif. Tissue Int. 91:196-203.
Ponnapakkam et al. "Monthly administration of a novel PTH-collagen binding domain fusion protein is anabolic in mice." 2011, Calcif. Tissue Int. 88:511-520.
Xian et al. "Matrix IGF-1 maintains bone mass by activation of mTOR in mesenchymal stem cells." 2012, Nature Medicine, 18:1095-1101.
International Search Report for PCT/IB2013/002349 dated Feb. 13, 2014.
Extended European Search Report for EP Application 13832369.6 based on PCT/IB2013/002349 issued May 6, 2016.
Yewle, J.N. et al. "Bifunctional bisphosphonates for delivering PTH (1-34) to bone mineral with enhanced bioactivity," Biomaterials, 2013, vol. 34:3141--3149.
Yewle, J.N. "Bifunctional bisphosphonates for delivering biomolecules to bone," University of Kentucky theses and dissertations, 2012.

\* cited by examiner

*Primary Examiner* — Xiaozhen Xie
(74) *Attorney, Agent, or Firm* — Gardner Groff Greenwald & Villanueva, PC

(57) ABSTRACT

Described herein is insulin, an insulin-like growth factor, parathyroid hormone, a fragment of parathyroid hormone, or a parathyroid hormone related protein that includes at least one bone targeting moiety, wherein the bone targeting moiety is covalently bonded to the peptide. Also described herein are the methods of making these compositions that prevent or treat conditions associated with bone loss and preventing bone fractures, and/or the inability to initiate de novo bone turnover and stimulate bone fracture repair.

16 Claims, 10 Drawing Sheets

SEQUENCE LISTING

```
<160> NUMBER OF SEQ ID NOS: 6

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 84
<212> TYPE: PRT
<213> ORGANISM: Homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 3
<211> LENGTH: 141
<212> TYPE: PRT
<213> ORGANISM: Homo sapiens

<400> SEQUENCE: 3

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60
```

```
Ala Glu Ile His Thr Ala Glu Ile Arg Ala Thr Ser Glu Val Ser Pro
 65                  70                  75                  80

Asn Ser Lys Pro Ser Pro Asn Thr Lys Asn His Pro Val Arg Phe Gly
                 85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Lys Arg
    130                 135                 140

<210> SEQ ID NO 4
<211> LENGTH: 21
<212> TYPE: PRT
<213> ORGANISM: Homo sapiens

<400> SEQUENCE: 4

Gly Ile Val Gln Gln Cys Cys Thr Ser Ile Cys Ser Leu Tyr Leu Gln
1               5                   10                  15

Glu Asn Tyr Cys Asn
            20

<210> SEQ ID NO 5
<211> LENGTH: 30
<212> TYPE: PRT
<213> ORGANISM: Homo sapiens

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 6
<211> LENGTH: 70
<212> TYPE: PRT
<213> ORGANISM: Homo sapiens

<400> SEQUENCE: 6

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
 65                  70
```

PARATHYROID HORMONE, INSULIN, AND RELATED PEPTIDES CONJUGATED TO BONE TARGETING MOIETIES AND METHODS AND MAKING AND USING THEREOF

CROSS REFERENCE TO RELATED APPLICATIONS

This application is a U.S. national phase application under 35 U.S.C. 371 of international application number PCT/IB2013/002349, filed Aug. 28, 2013, which claims priority upon U.S. provisional application Ser. No. 61/693,818, filed Aug. 28, 2012. These application are hereby incorporated by reference in its entirety for all of their teachings.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Conditions that cause loss of bone mass and micro-architectural deterioration of bone structure affect many worldwide. For example, 44 million people age 50 or older are affected by osteoporosis in the United States alone. In addition, other conditions including, but not limited to, Paget's disease, osteolytic tumors, Rheumatoid Arthritis, Psoriatic Arthritis, Ankylosing Spondylitis, Osteoarthritis, osteopenia including drug induced osteopenia, and hypercalcemia also cause loss of bone mass and affect hundreds of millions of people worldwide.

These conditions predispose those suffering from these maladies to enhanced bone fragility and risk of fracture. Each condition has various etiologies such as congenital conditions, malnutrition, or various additional factors. For example, osteoporosis alone has at least three etiologies. The etiologies for osteoporosis have been established based on predisposing factors and clinical presentation, namely: postmenopausal (type I), senile (type II), and secondary (type III) osteoporosis. In all types, the declining ability of the bone remodeling machinery results in bone fragility. Type I postmenopausal osteoporosis (PMOP) occurs in women 51-75 years of age, in which, estrogen deficiency shifts bone remodeling to favor bone resorption over bone formation, which results in a net bone loss. Type II senile osteoporosis affects women at about twice the rate as men, and occurs from ages 75 to 90 years. Type III or secondary osteoporosis is caused by medications, cancers, endocrine disorders, chronic liver or kidney diseases, and additional conditions. The net result for each type of osteoporosis is the insidious loss of bone mass and the predisposition to traumatic bone fracture.

Numerous treatments have been administered to patients with these conditions; these treatments include the administration of hormone replacement therapy, antiresorptive agents, and immunosuppressants including monoclonal antibodies. However, administering therapeutic levels of these treatments often result in various side effects. For example, some treatments have been linked to various cancers, bone necrosis or osteonecrosis, and other unwanted side effects. Therefore, it is generally difficult to efficiently treat or prevent conditions that cause bone loss with the currently known compositions and methods.

Parathyroid hormone (PTH), also called parathormone or parathyrin, is a 84-residue peptide hormone secreted by chief cells of the parathyroid glands. It plays an important role on regulating extracellular calcium homeostasis, by acting upon the parathyroid hormone receptors (1 and 2) in bone, kidney, central nervous system, pancreas, testis and placenta. By binding to osteoblasts, PTH increases their expression of receptor activator of nuclear factor kappa-B ligand (RANKL) meanwhile decreases their expression of osteoprotegin (OPG), the latter is an inhibitor of interaction between RANKL and RANK. As a result, the binding of RANKL to RANK promotes bone resorption by forming new osteoclasts. hPTH (1-34) is a N-terminal fragment of PTH, and it is composed of 34 amino acid, expressing complete biological activity of PTH. However, according to the concentration in vivo, hPTH (1-34)/PTH can demonstrate exactly the opposite two bio-functions that high and sustained doses lead to bone resorption, but low doses lead to bone formation, therefore, hPTH (1-34)/PTH could be applied for treatment of bone-disease such as osteoporosis. However, similar to salmon calcitonin, the short half-life of hPTH (1-34)/PTH in vivo restricts its clinical application, although a therapeutic osteoporosis medicine, recombinant PTH (teriparatide, Forteo, Eli Lilly) has been approved by FDA almost 10 years ago The insulin-like growth factors (IGFs) are proteins with high sequence similarity to insulin. The insulin-like growth factor-1, (IGF-1, also named somatomedin C), composed by 70 amino acids, has growth-promoting effects on cells including bone cells, which is being tested in clinical trials of osteoporosis, as one of approved agents by FDA. Similar to PTH, IGF-1 is also cleared rapidly through the kidney, but when bound to insulin-like growth factor binding protein-3 (IGFBP-3), the resultant recombinant complex evades renal clearance.

SUMMARY

Described herein is insulin, an insulin-like growth factor, parathyroid hormone, a fragment of parathyroid hormone, or a parathyroid hormone related protein that includes at least one bone targeting moiety, wherein the bone targeting moiety is covalently bonded to the peptide. Also described herein are the methods of making these compositions that prevent or treat conditions associated with bone loss and methods of preventing bone fractures. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
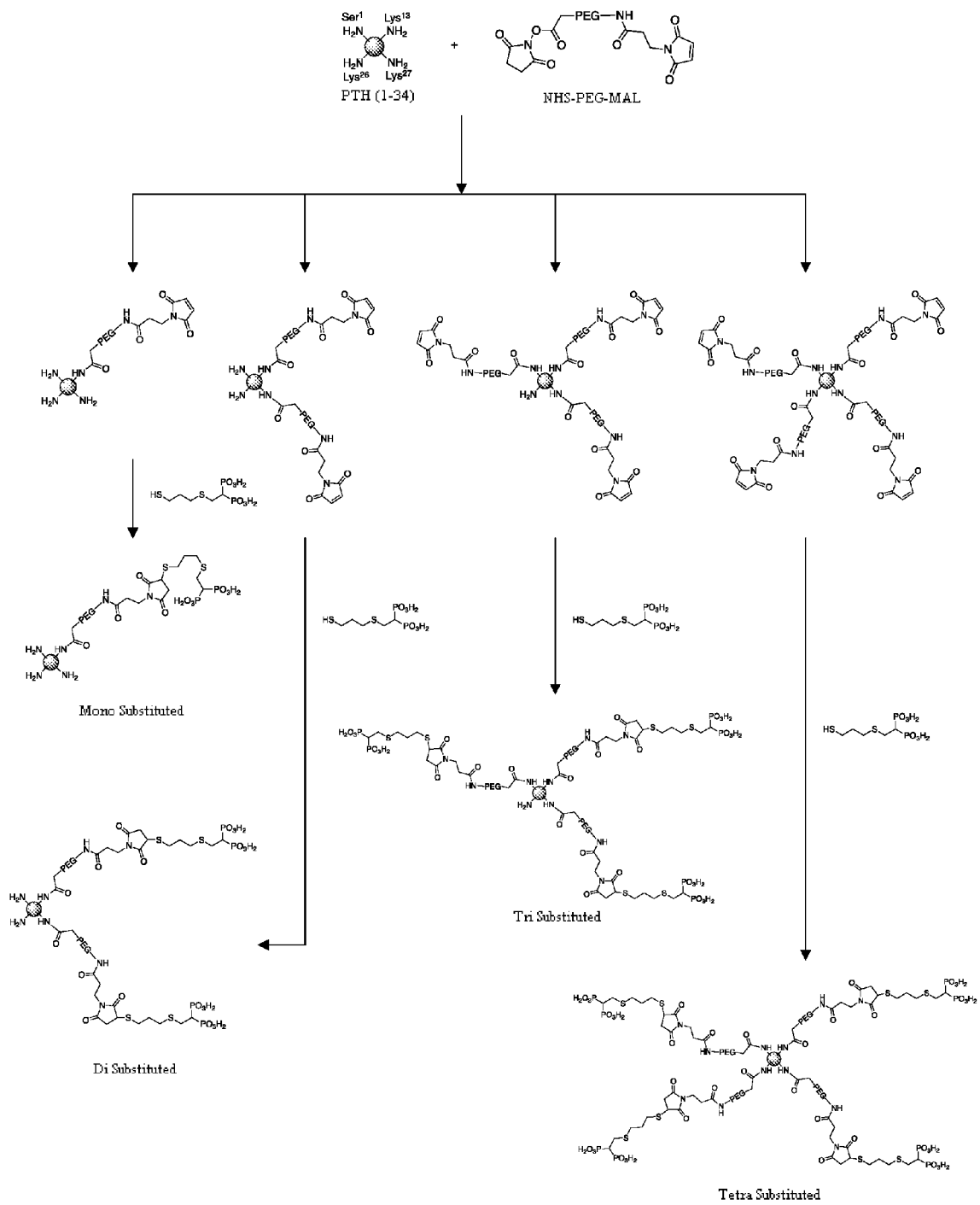
FIG. 1 shows a reaction scheme for the synthesis of parathyroid hormone with a bone targeting compound covalently attached to it.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted with a group" means that the group may or may not be present in the compounds and compositions described herein.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Subject" refers to mammals including, but not limited to, humans, non-human primates, sheep, dogs, rodents (e.g., mouse, rat, etc.), guinea pigs, cats, rabbits, cows, and non-mammals including chickens, amphibians, and reptiles, who are at risk for or have been diagnosed with a condition that causes bone loss and benefits from the methods and compositions described herein.

When describing variants in proteins or peptides, the term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 65%, 70%, 75%, 80%, 85%, 90%, 95%, 96%, 97%, 98%, or 99% homology to a reference sequence.

The terms "homology," "identity or identical," and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a targeting moiety that contains at least one —SH group can be represented by the formula W—SH, where W is the remainder (i.e., residue) of the targeting moiety.

"Bone targeting moiety" refers to any chemical compound, peptide, or nucleic acid that has an affinity for bone mineral, matrix and/or cells, including bone hydroxyapatite, osteocytes, osteoblasts, osteoclasts or any combination thereof and is capable of selectively targeting bone mineral, matrix and/or cells including hydroxyapatite, osteocytes, osteoblasts, osteoclasts, or any combination thereof over other cells and tissues. Structural information regarding the bone targeting moieties used herein is provided below.

The term "polyether group" as used herein is a group having the formula —[(CHR)$_n$O]—, where R is hydrogen or a lower alkyl group, and n is an integer of from 1 to 20. The molecular weight can vary. In one aspect, the molecular weight is from 500 to 20,000, or from 2,000 to 10,000. Examples of polyether groups include, but are not limited to, polyethylene oxide, polypropylene oxide, and polybutylene oxide. The polyether group can also be a block copolymer such as, for example, a polyethylene/polypropylene block copolymer The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkylene group" as used herein is a branched or unbranched unsaturated hydrocarbon group of 1 to 24 carbon atoms such as methylene, ethylene, propene, butylene, isobutylene and the like.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, halo, hydroxy, alkylthio, arylthio, alkoxy, aryloxy, amino, mono- or di-substituted amino, ammonio or substituted ammonio, nitroso, cyano, sulfonato, mercapto, nitro, oxo, alkyl, alkenyl, cycloalkyl, benzyl, phenyl, substituted benzyl, substituted phenyl, benzylcarbonyl, phenylcarbonyl, saccharides, substituted benzylcarbonyl, substituted phenylcarbonyl and phosphorus derivatives. The aryl group can include two or more fused rings, where at least one of the rings is an aromatic ring. Examples include naphthalene, anthracene, and other fused aromatic compounds.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

Compositions

Described herein are parathyroid hormone or insulin that include at least one bone targeting moiety, wherein the targeting moiety is covalently bonded to the peptide sequence, and wherein the composition is neutral or a pharmaceutically acceptable salt or ester thereof. In one aspect, the compounds described herein are a peptide sequence having at least one amino proton in the peptide sequence that is substituted with a group having the formula I:

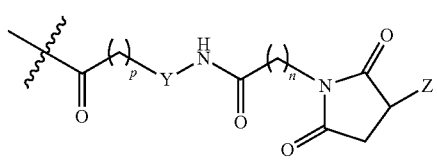

wherein the peptide sequence is insulin or parathyroid hormone;
Y is a residue of a polyether group;

Z is a residue of a bone targeting group;
n is from 1 to 10; and
p is from 1 to 10,
or the pharmaceutically acceptable salt or ester thereof.

Parathyroid hormone (PTH) (SEQ ID NO. 2), also called parathormone or parathyrin, is a 84-residue peptide hormone secreted by chief cells of the parathyroid glands. PTH plays an important role on regulating extracellular calcium homeostasis, by acting upon the parathyroid hormone receptors in bone, kidney, central nervous system, pancreas, testis and placenta. By binding to osteoblasts, PTH increases their expression of receptor activator of nuclear factor kappa-B ligand (RANKL). Meanwhile PTH decreases their expression of osteoprotegin (OPG), the latter is an inhibiter of interaction between RANKL and RANK. As a result, the binding of RANKL to RANK promotes bone resorption by forming new osteoclasts. hPTH (1-34) (SEQ ID NO. 1) is a N-terminal fragment of PTH, and it is composed of 34 amino acid, expressing complete biological activity of PTH. In one aspect, hPTH (1-34) (SEQ ID NO. 1), (PTH) (SEQ ID NO. 2), as well as PTHrP (1-141) (SEQ ID NO 3) can be used herein.

Insulin can effect as well vascular compliance and cognition. Insulin signaling in bone has been linked to diabetes associated bone disorders (e.g., diabetic osteoporosis) as well overall glucose metabolics. Insulin can react with bone cell populations. This is desirable, as this will may initiate or assist with bone re-modeling. The compounds described herein assist insulin by directing their action to bone cells on the bone surfaces and by not competing with other tissues that have insulin-receptors. Thus, the compounds described herein can improve the ability of insulin to react with osteoclasts, osteoblasts and osteocytes present in bone, which improves the action of insulin upon bone cells in various bone diseases. In one aspect, the insulin comprises two peptide sequences, wherein each peptide sequence is at least 90% identical to SEQ ID NOS 4 and 5. In another aspect, the insulin is human insulin (1-51). In another aspect, insulin-like growth factor-1, (IGF-1, also named somatomedin C) having SEQ ID NO 6 (Accession No. 0912651A) can be used herein.

The polyether group Y imparts several benefits when linked to parathyroid hormone or insulin. The polyether group can increase the molecular weight of the compound, which can increase the half-life of the compound and decrease the immunogenicity of the compound. The polyether group can also increase the solubility of the compounds. In addition, the polyether group can increase the stability of parathyroid hormone and insulin while decreasing the tendency of parathyroid hormone and insulin to aggregate. In some aspects, the polyether groups can also decrease immunogenicity of parathyroid hormone and insulin. In one aspect, Y is a polyethylene group. In another aspect, Y is a polyethylene group having a molecular weight from 1,000 to 10,000.

The compositions described herein can include a bone targeting compound (Z), wherein the bone targeting compound can include a bisphosphonate containing compound. In one aspect, the bisphosphonate containing compound has the formula II

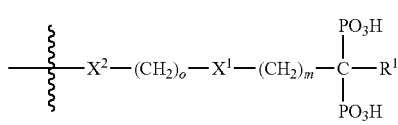

wherein $R^1$ is hydrogen, a hydroxyl group, an alkyl group, an alkylene group, an amine group, a thiol group, or an aryl group;

$X^1$ and $X^2$ are, independently, O, S, or $NR^3$, wherein $R^3$ is hydrogen, an alkyl group, an aryl group, or a cycloalkyl group; and m and o are, independently, from 1 to 8.

In one aspect, $R^1$ is hydrogen, $X^1$ and $X^2$ are S, m is 1, and o is 3[{2-[(3-mercaptopropyl)thio]ethane-1,1-diyl}bis (phosphonic acid)].

In another aspect, the bisphosphonate containing compound includes, but is not limited to, a residue of etidronic acid, clodronic acid, tiludronic acid, pamidronic acid, neridronic acid, olpadronic acid, alendronic acid, ibandronic acid, zolendronic acid, risedronic acid, or a combination thereof. In some aspects, the bone targeting moiety is a residue of {2-[(3-mercaptopropyl)thio]ethane-1,1-diyl}bis (phosphonic acid). In this aspect, the targeting moiety is covalently attached to the molecule via the sulfur atom.

In some aspects, the parathyroid hormone and insulin can include at least one, two, three, four, five, six, seven, eight, nine, or ten, reactive amino groups (i.e., amino proton that is substituted with a group having formula I). For example, the amino protons of $Ser^1$, $Lys^{13}$, $Lys^{26}$, and $Lys^{27}$ in hPTH (SEQ ID NO 1) can be substituted with a group having the formula I. Any amino acid present in parathyroid hormone or insulin can be substituted with a group having the formula I.

Any of the compounds described herein can be the pharmaceutically-acceptable salt or ester thereof. In one aspect, pharmaceutically-acceptable salts are prepared by treating the free acid with an appropriate amount of a pharmaceutically-acceptable base. Representative pharmaceutically-acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

In another aspect, if the compound possesses a basic group, it can be protonated with an acid such as, for example, HCl, HBr, or $H_2SO_4$, to produce the cationic salt. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

Ester derivatives are typically prepared as precursors to the acid form of the compounds. Generally, these derivatives will be lower alkyl esters such as methyl, ethyl, and the like. Amide derivatives —$(CO)NH_2$, —(CO)NHR and —(CO)$NR_2$, where R is an alkyl group defined above, can be prepared by reaction of the carboxylic acid-containing compound with ammonia or a substituted amine.

The compounds described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular sites and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice.

The pharmaceutical composition can be administered in a number of ways depending on whether local or systemic treatment is desired, and on the area to be treated. Administration can be topical, including ophthalmic and intranasal, or administration may be sub-cutaneous, transdermal, transcutaneous, intravenous or intraperitoneal.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

Methods for Making Compositions

Further described herein are methods of making the compositions having parathyroid hormone or insulin covalently bonded to a bone targeting moiety. The method generally involves (1) reacting at least one amine group present in parathyroid hormone or insulin sequence with a compound having the formula III, where LG is a leaving group, to produce a first intermediate; and

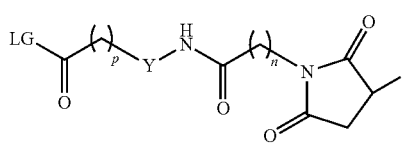

(2) reacting the first intermediate with a bisphosphonate containing compound.

Figure 2:
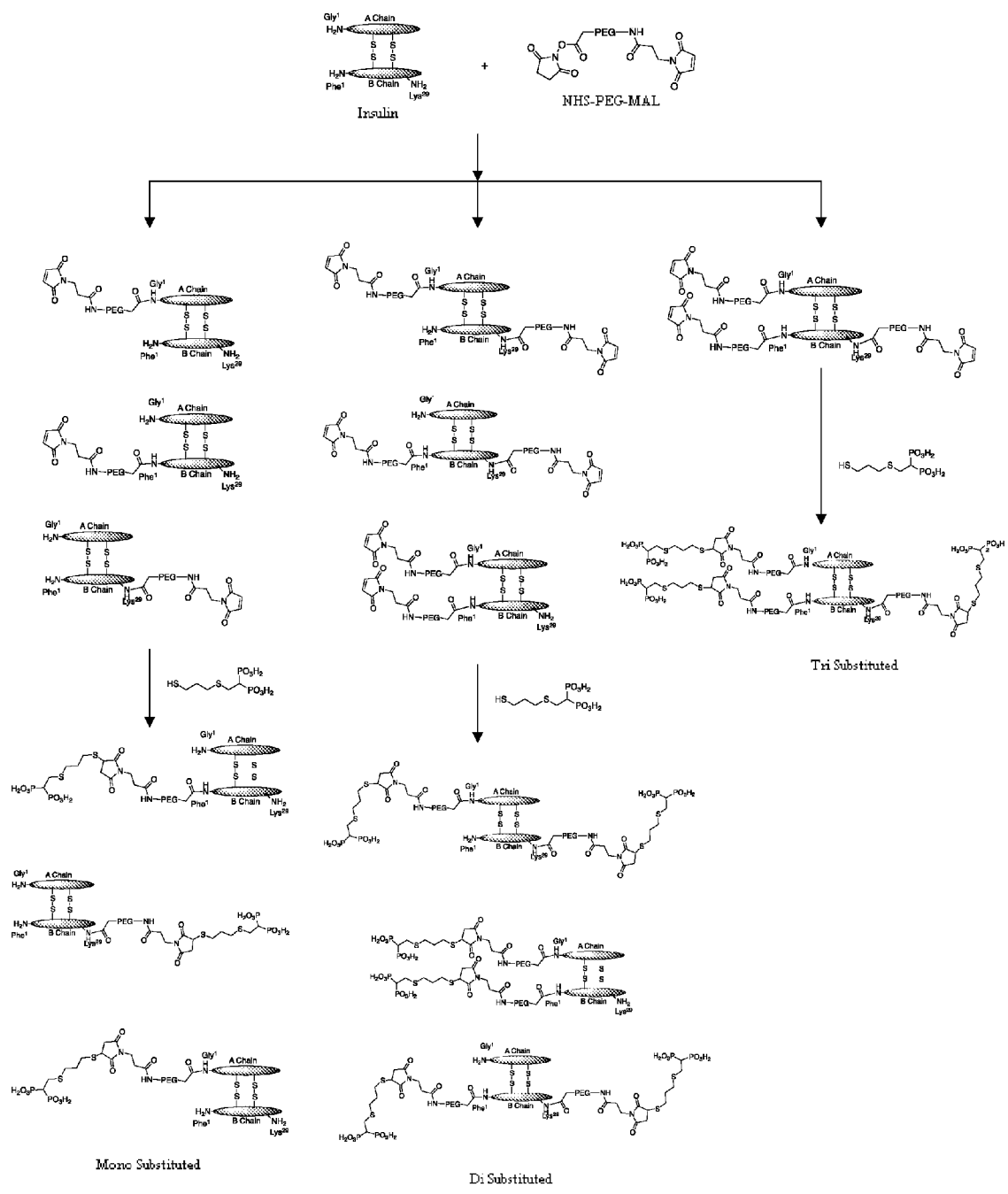
FIG. 2 shows a reaction scheme for the synthesis of insulin with a bone targeting compound covalently attached to it.
Figure 3A:
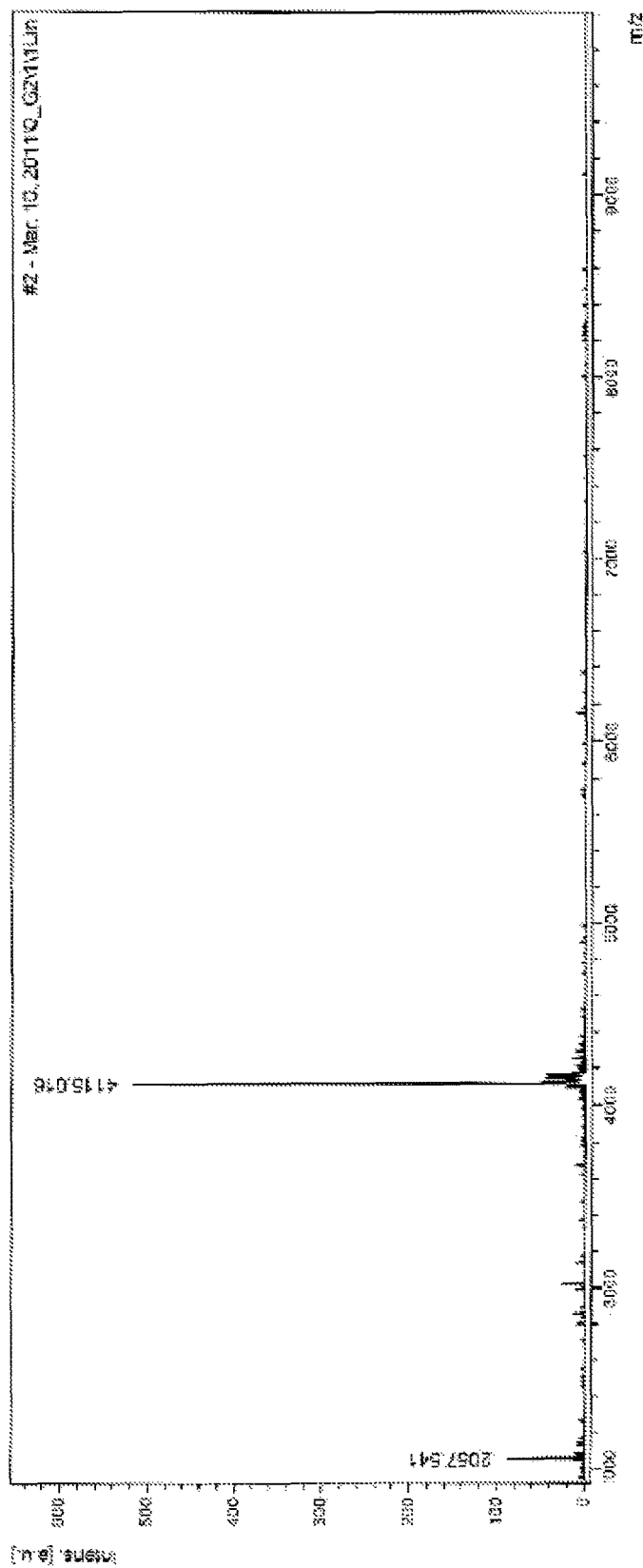
FIG. 3 shows MALDI-ToF results of (a) hPTH (1-34), (b) and (c) $PEG_{3500}$, and (d) and (e) hPTH (1-34)-$PEG_{3500}$.
Figure 3B:
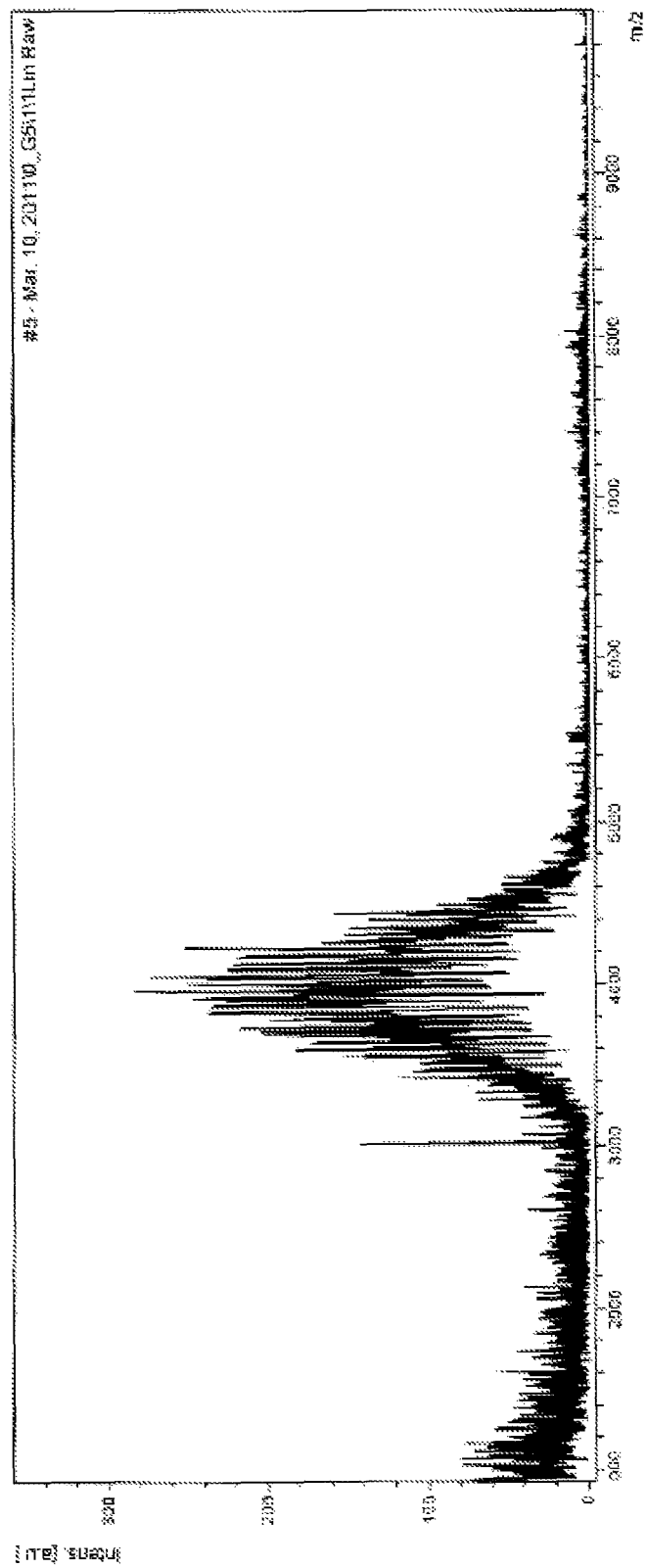
Figure 3C:
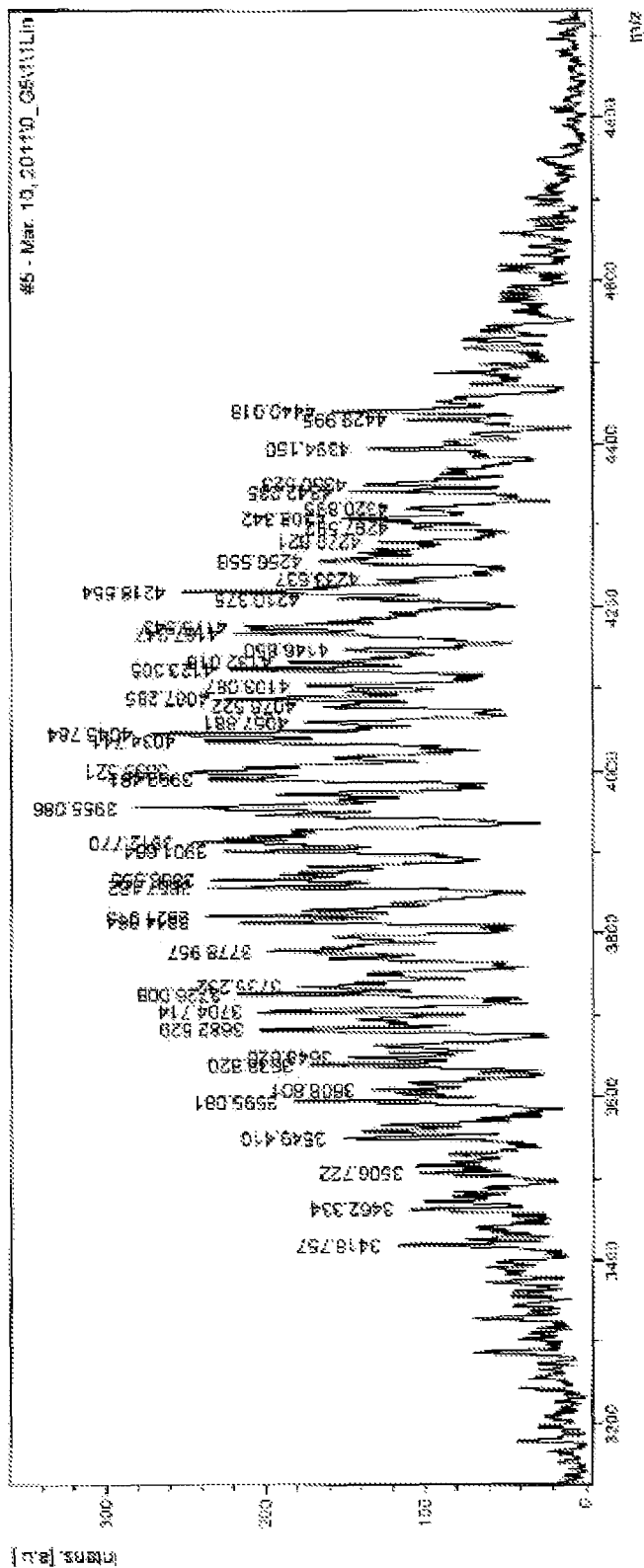
Figure 3D:
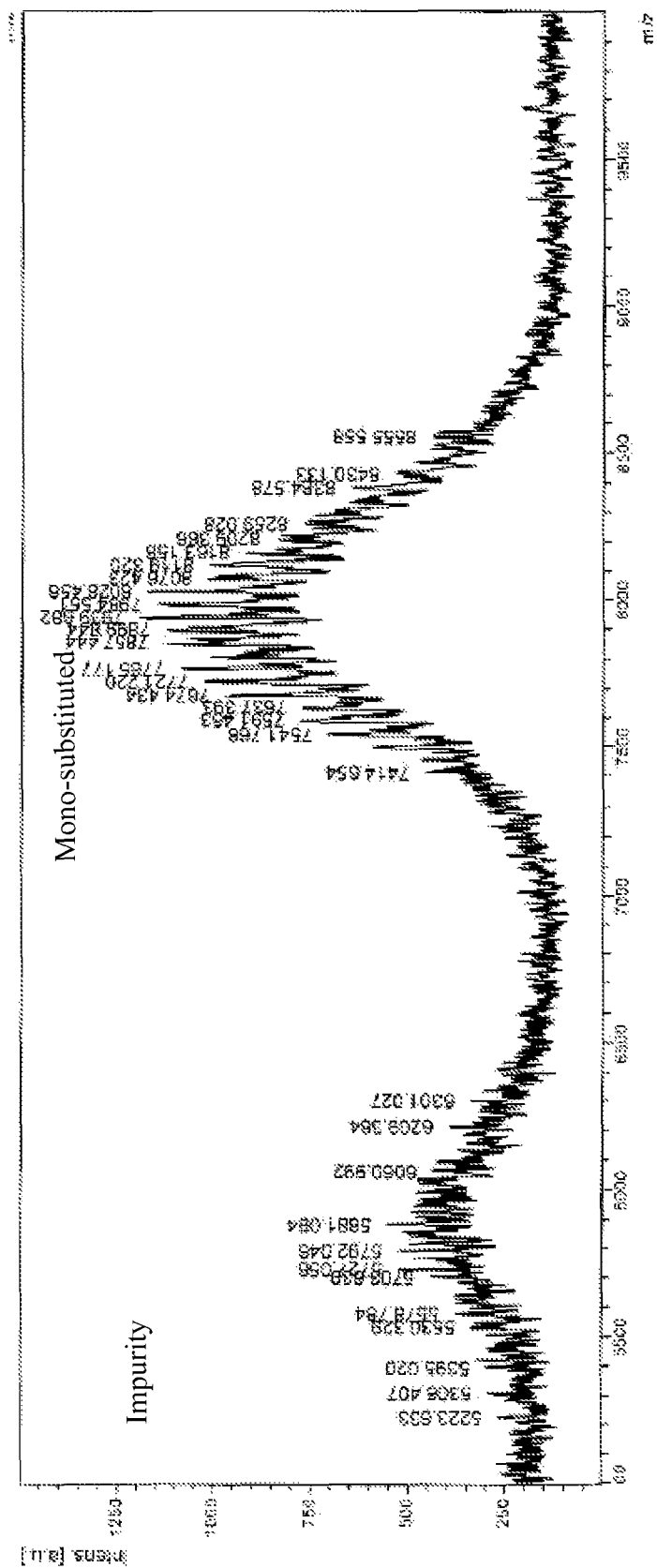
Figure 3E:
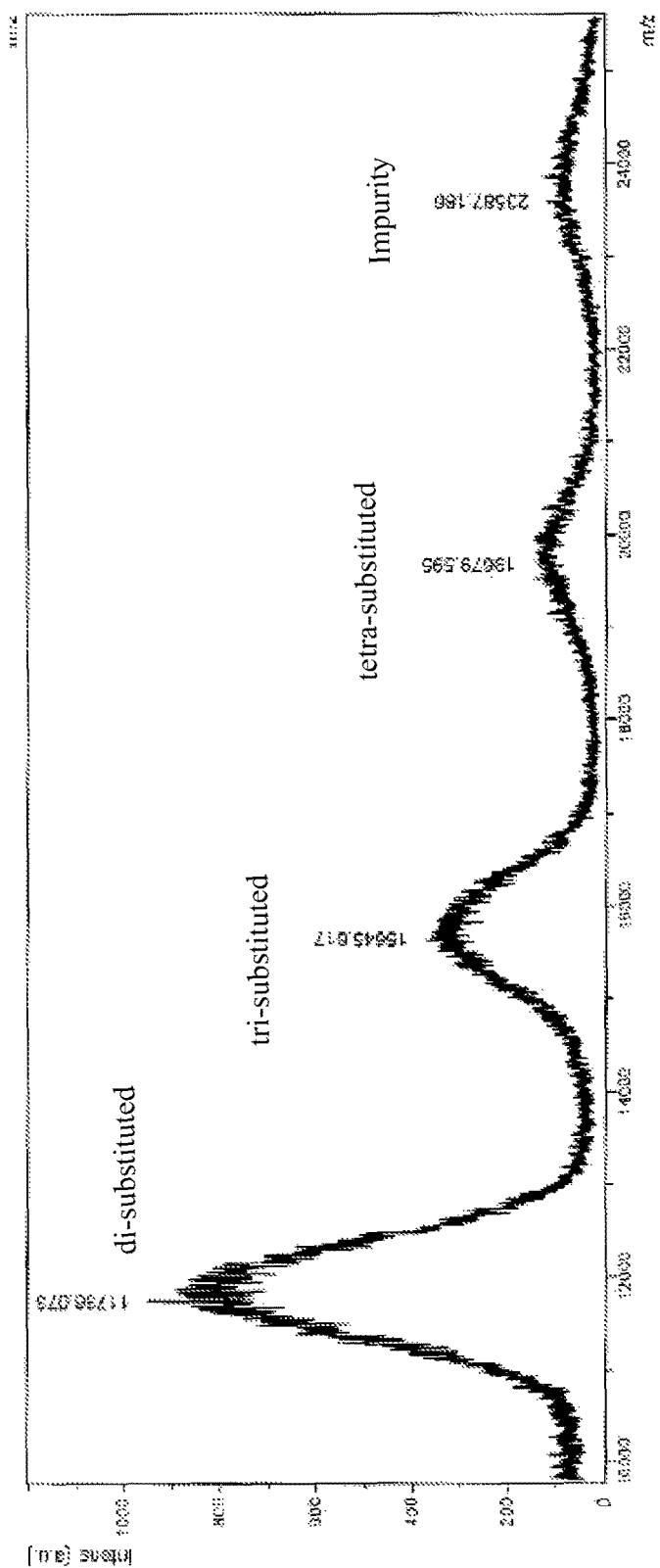

Exemplary procedures for making the compounds described herein are provided in FIGS. 1 and 2 as well as the Examples. In one aspect, the compound having the formula III is NHS-PEG-MAL (FIG. 1) manufactured by JenKem Technology. In this method, the bone targeting moiety can include any of the bisphosphonate compounds described above. For example, the bisphosphonate compound can include a thiol containing bisphosphonate compound.

The amount of compound having the formula III used relative to parathyroid hormone or insulin will determine the number of groups having the formula I that will be attached to the peptide. For example, a particular ratio, for example a mol/mol ratio, of parathyroid hormone or insulin to the compound having the formula III can vary. In addition, reaction times can be adjusted to form various intermediates that can include mono-substituted, bi-substituted, and tri-substituted intermediates as shown in FIGS. 1 and 2. In this aspect, the ratio of parathyroid hormone or insulin to compound having the formula III can include but is not limited to a 1:3, a 1:5, a 1:7, or a 1:10 mol/mol ratio. In some aspects, the parathyroid hormone or insulin and compound having the formula III are reacted for a period of time including, but not limited to, 1, 2, 3, 4, 5, 10, 15, 20, 25, 35, 40, 45, 50, 60, 65, 70, 75, 80, 85, or 90 minutes at about room temperature.

In some aspects, when the parathyroid hormone or insulin and compound having the formula III are reacted, organic solvents, organic solvents mixed with aqueous solvents including buffers, or any combination thereof can be added. Organic solvents can include, but are not limited to, dimethyl sulfoxide (DMSO), trimethylformamide (TMF), dimethylformamide (DMF), chloroform, triethylamine (TEA), and alcohols. In some aspects, the organic solvent can be added to the reaction at a 0.01% v/v, 0.02% v/v, 0.03% v/v, 0.04% v/v, 0.05% v/v, 0.1% v/v, 0.2% v/v, 0.3% v/v, 0.4% v/v, 0.5% v/v, 0.6% v/v, 0.7% v/v, 0.8% v/v, 0.9% v/v, 1.0% v/v, 1.5% v/v, 2.0% v/v or more final concentration of the organic solvent. Aqueous solvents and buffers can include, but are not limited to, water, phosphate buffers, carbonate buffers, and acetate buffers. In one aspect, triethylamine (TEA) can be used. In some aspects, the overall final concentration of TEA can include but is not limited to 0.1% v/v. In another aspect, TEA in dimethylformamide can be used.

In some aspects, either when reacting the parathyroid hormone or insulin and compound having the formula III or after the reaction, the pH can be adjusted. In some aspects, the pH should be alkaline, wherein the pH ranges from 6.0 to 14.0, 7.0 to 14.0, from 7.0 to 12.0, from 7.0 to 10.0, from 7.0 to 9, from 7.0 to 8.0, or from 7.5 to 8.0. In certain aspects, the pH is from 7.0 to 9. In some aspects, when TEA is present, it acts as an organic pH modifier to make the pH more alkaline.

After the reaction of the parathyroid hormone or insulin and compound having the formula III to produce the first intermediate, the intermediate is reacted with a bone targeting moiety, which includes a thiol containing bisphosphonate compound, to form at least one of the compositions described herein. In some aspects, a particular ratio, for example a mol/mol ratio, of the intermediate to bone targeting moiety can be utilized to form one of the compositions described herein. In addition, reaction times can be adjusted to form various compositions that can include mono-substituted, bi-substituted, and tri-substituted compositions. In this aspect, the ratio of the intermediate to bone targeting moiety can include but is not limited to a 1:3, a 1:5, a 1:7, a 1:10, or a 1:20 mol/mol ratio. In some aspects, the intermediate is reacted with a bone targeting moiety, which can include a bisphosphonate containing compound, for 1 minute to 24 hours (or longer if desired) at room temperature if desired to form a peptide-linker-bone targeting moiety composition. In certain aspects, the reaction temperature may be cooler or warmer than room temperature if desired. In certain aspects, a longer reaction time may be desired, and the intermediate is reacted with the bone targeting moiety at different times and different temperatures. For example, if a longer reaction time is desired, the intermediate can be reacted with the bone targeting moiety for 1 to 2 hours at room temperature and then stored at 4° C. for up to 22 hours.

In some aspects, either when reacting the intermediate with the bone targeting moiety or after the formation of the parathyroid hormone or insulin conjugated to a bone targeting moiety, the pH can be adjusted. In some aspects, buffers including, but not limited to, phosphate buffers, acetate buffers, or a combination thereof can be added. In some aspects, the pH can be adjusted to a pH ranging from 6.0 to 8.5, from 6.5 to 7.5, from 6.5 to 7.5, or from 6.5 to 7.0. In some aspects, the pH can be adjusted to pH 6.8. Additional, non-limiting, procedures for making the compositions described herein are provided in the examples section and the figures.

Applications

In some aspects, the compositions described herein can be administered to a subject to treat or prevent a condition that causes loss of bone mass, or to initiate the de novo turnover of bone. The subject can either be experiencing bone loss or be at risk for such a condition, or conversely may be unable to initiate bone remodeling. To determine whether a subject is experiencing metabolic bone disease, numerous tests, such as bone density testing, a battery of genetic tests, a subject's medical history, and the subject's family medical history, can be used to make this determination. In one aspect, these compositions are administered to a subject, wherein the subject includes a mammal. In this aspect, the subject can include a human.

In certain aspects, the condition may be linked to congenital conditions or improper diet. In this aspect, an osteoclast may remove bone tissue (i.e., bone resorption) more quickly than new bone cells and tissue can be produced. Conversely, an osteoblast may not deposit or mineralize adequate bone tissue (i.e., bone formation). The overall effect leads to imbalanced bone turnover that may result in osteopenia and/or focal osteosclerosis. In some aspects, the condition includes, but is not limited to, osteoporosis, Paget's disease, osteolytic tumors, Rheumatoid Arthritis, Psoriatic Arthritis, Ankylosing Spondylitis, Osteoarthritis, osteoporosis, osteosclerotic tumors, hypercalcemia, osteopenia including drug induced osteopenia, or a combination thereof. In some aspects, the condition causes osteoclast mediated resorptive bone loss.

In certain aspects, bone loss can be reduced by contacting the bone with the compositions described herein. In other aspects, the compositions described herein can be administered to a subject to prevent bone fractures and to strengthen bones. In other aspects, the compositions described herein can be administered to a subject to stimulate de novo bone turnover and to improve bone balance.

In each of these aspects, administration may be via oral administration, injection including intramuscular or subcutaneous injection, transdermal or transcutaneous routes or via nasal administration.

In some aspects, the subject would benefit from the administration of the compositions described herein because of the increased targeting and localization of the composition, to bone and the increased retention time of the composition, which includes PTH and/or Insulin, in and/or on the bone. This increased localization and retention time (i.e., enhanced drug delivery) could result in additional positive effects such as increasing bioavailability of PTH and/or Insulin to bone cells, administering lower dosages of the peptide bisphosphonate conjugate when compared to administering PTH and/or Insulin or bisphosphonate drugs alone, improved inhibition or reduction of osteoclast mediated resorptive bone loss when compared to administering PTH and/or Insulin alone, and reducing the side-effects associated with administering PTH and/or Insulin or bisphosphonate drugs alone.

In the case when the peptide is insulin, the compounds described herein can enhance the ability of insulin to treat a subject with diabetes, by utilizing the mineralized skeleton as a drug depot-scaffold from which to effect the controlled and/or sustained release of Insulin to the systemic circulation, thereby increasing the circulating half-life and terminal residence of Insulin after the initial dose.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials hPTH (1-34) was purchased from Bachem Americas, Inc. (USA). Maleimide PEG NHS Ester ($PEG_{3500}$, MW 3500) was purchased from JenKem Technology (USA). Other reagents and solvents were purchased from Sigma-Aldrich without further purification. Thiol-bisphosphonate (Thiol-BP, MW 296) was purchased from Surfactis Technologies (France).

Synthesis and Characterization of Parathyroid Hormone-Bone Targeting Compound

A mixture of 150 μL hPTH (1-34) solution (9 mg/mL, DMSO) and 80 μL Maleimide-PEG-NHS Ester solution (55 mg/mL, DMSO) was vortexed at room temperature for 45 min (speed 1), followed by mixing with 1.3 mL Thiol-BP solution (25.7 mg/mL, 100 mM pH 7.0 phosphate buffer). After shaking gently until uniform, the mixture was stored in the dark at room temperature for 2 hours. The reaction scheme is depicted in FIG. 1.

Figure 4:
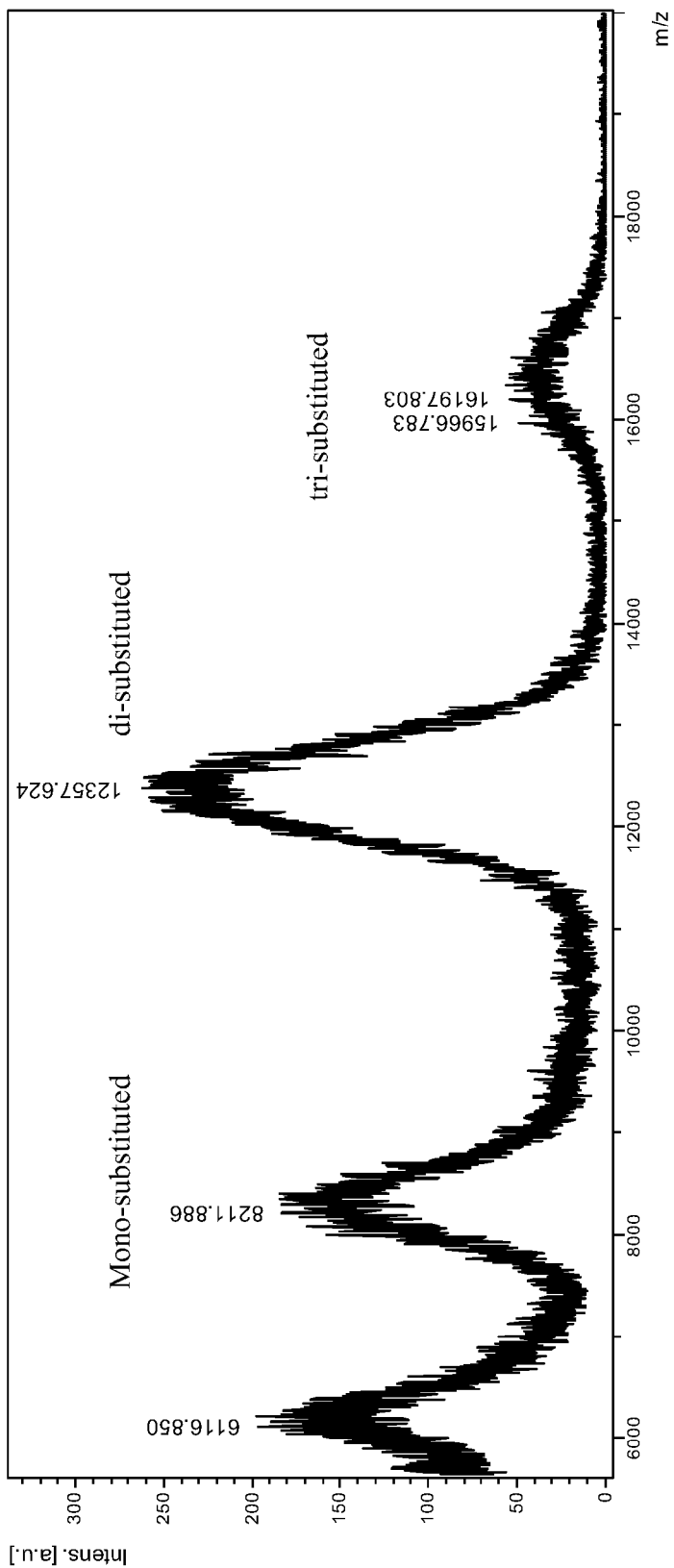
FIG. 4 shows MALDI-ToF results of hPTH (1-34)-$PEG_{3500}$-BP.

There are four potential conjugating sites in hPTH (1-34): $Ser^1$, $Lys^{13}$, $Lys^{26}$, and $Lys^{27}$. MALDI-ToF shows that the peak at 4115, indicating hPTH (1-34) disappeared in the resultant reaction solution, and 6 new peaks were observed: the peaks of average molecular weight 7940, 11736, 15646, 19680 represented mono-(cal. 7600), di- (cal. 11115), tri- (cal. 14600), tetra-substitution (cal. 18715), respectively, and the other impurities had average MW of 5881 and 23587 (FIG. 3). After biphosphonation, a mixture of mono-, di-, tri-PEGylated hPTH(1-34)-PEG-BP were confirmed by MALDI-ToF, in comparison to hPTH(1-34)-PEG, the increased mass (from 7940, 11736, 15646 to 8219, 12358, 16198) showed that biphosphonation occurred (FIG. 4).

Figure 5:
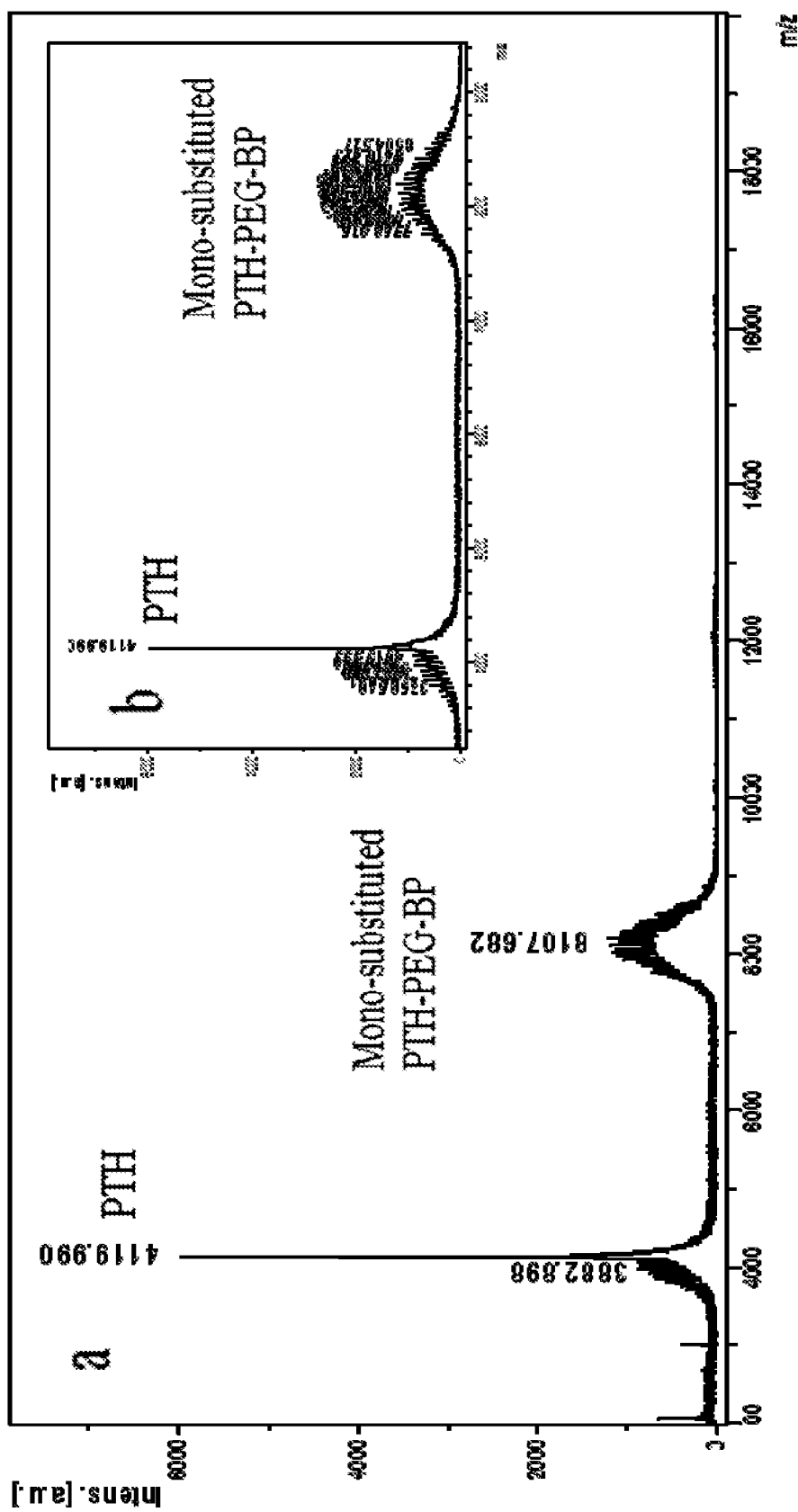
FIG. 5 shows MALDI-ToF results of HPLC-purified, mono-substituted hPTH (1-34)-$PEG_{3500}$-BP. (a) 0-20,000 Da scan. (b) Magnified view of region of interest.

Mono-substituted PTH-PEG-BP was HPLC purified. Identity of the isolated compound was confirmed using MALDI-TOF. The mass of interest was 8107 Da (FIG. 5).

Change in Bone Volume

Sixty female rats were divided into five groups and evaluated using the ovariectomy procedure (OVX): control (sham-operated; n=12), ovariectomy with bisphosphonate treatment (OVX-BP; n=12), OVX with teriparatide treatment (OVX-PTH; daily; n=12), OVX with daily BP-PEG-PTH treatment (n=12), and OVX with weekly BP-PEG-PTH treatment (n=12), where BP is 2-[(3-mercaptopropyl)thio]ethane-1,1-diyl}bis(phosphonic acid). Rats were ovariectomized at week 0 and the control group underwent a sham ovariectomy. Rats were left untreated for 8 weeks after surgery to allow for osteopenia to develop. After 8 weeks, rats in the OVX-PTH group received daily subcutaneous injections of PTH (60 μg/kg/day) for 8 weeks. Rats in the OVX-BP group received daily doses of bisphosphonate. Rats in the OVX-BP-PEG-PTH daily group received daily subcutaneous injections of BP-PEG-PTH (60 μg/kg/day). Rats in the OVX-BP-PEG-PTH weekly group received weekly subcutaneous injections of BP-PEG-PTH (60 μg/kg/week).

Figure 6:
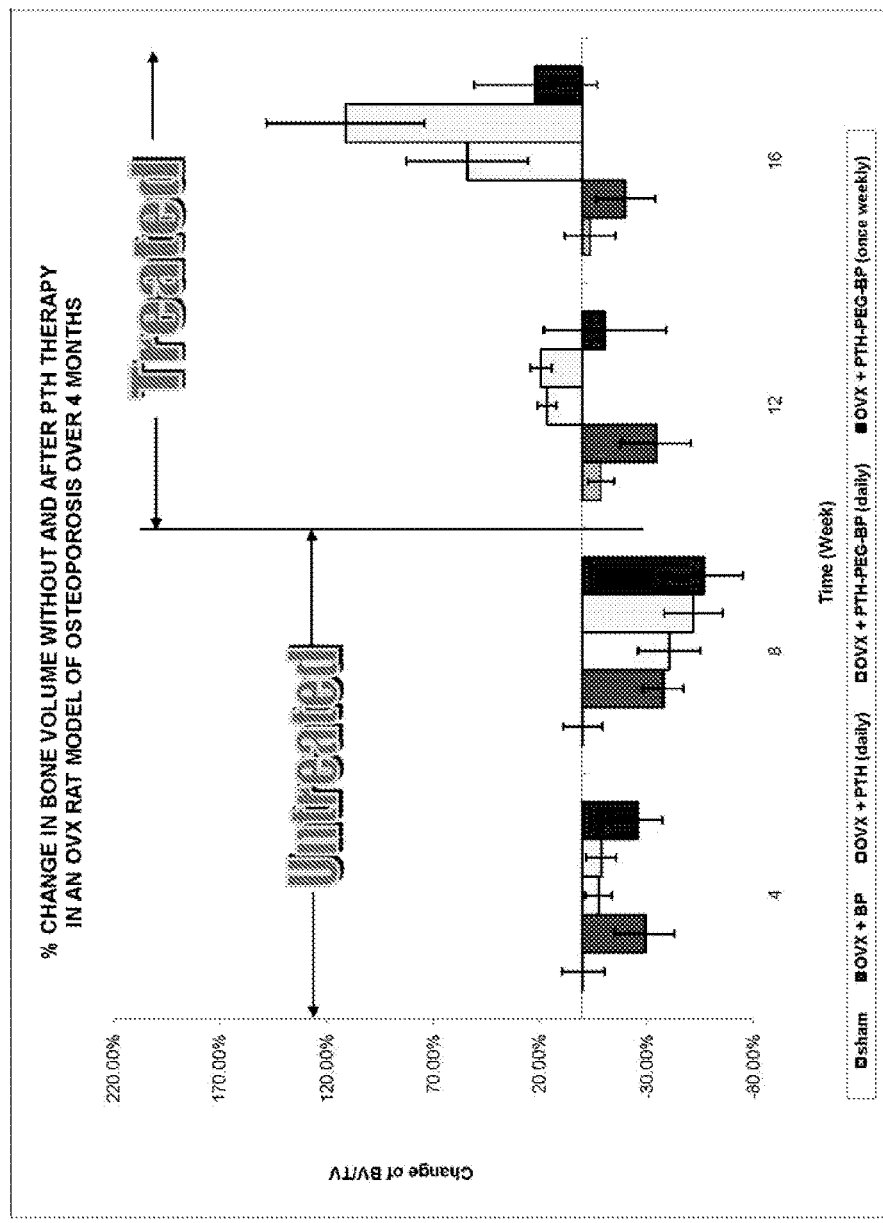
FIG. 6 shows % change in bone volume before and after PTH and BP therapy in an ovariectomied rat model of osteoporosis over a period of four months.

In vivo change in bone volume was measured by microcomputed tomography (microCT). Rats in the OVX-BP- PEG-PTH daily group exhibited the greatest increase in bone volume at 16 weeks post-ovariectomy (FIG. 6).

Synthesis of Insulin-Bone Targeting Compound

A mixture of 150 μL insulin solution (16 mg/mL, DMSO) and 80 μL Maleimide-PEG-NHS Ester solution (55 mg/mL, DMSO) was vortexed at room temperature for 45 min (speed 1), followed by mixing with 1.3 mL Thiol-BP solution (25.7 mg/mL, 100 mM pH 7.0 phosphate buffer). After shaking gently until uniform, the mixture was stored in the dark at room temperature for 2 hours. The reaction scheme is depicted in FIG. 2.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

---

What is claimed:

1. A compound comprising a peptide sequence, wherein at least one amino proton in the peptide sequence is substituted with a group having the formula I:

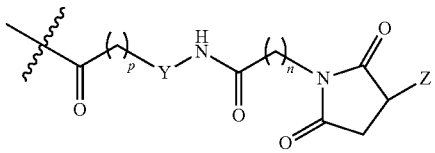

wherein the peptide sequence is a mammalian parathyroid hormone, a fragment of a mammalian parathyroid hormone, or a mammalian parathyroid hormone-related protein;
Y is a polyether group;
Z is a bisphosphonate-containing group;
n is from 1 to 10; and
p is from 1 to 10,
or the pharmaceutically acceptable salt or ester thereof.

2. The compound of claim 1, wherein the mammalian parathyroid hormone is a peptide sequence at least 90% identical to SEQ ID NO: 2.

3. The compound of claim 1, wherein the fragment of the mammalian parathyroid hormone is a peptide sequence at least 90% identical to SEQ ID NO: 1.

4. The compound of claim 1, wherein the mammalian parathyroid hormone-related protein is a peptide sequence at least 90% identical to SEQ ID NO: 3.

5. The compound of claim 1, wherein Y is polyethylene glycol, polypropylene glycol, or a polyethylene/polypropylene block copolymer.

6. The compound of claim 1, wherein Y is —$(OCH_2CH_2)_q$-, wherein q is from 20 to 200.

7. The compound of claim 1, wherein the bisphosphonate-containing group has the formula II:

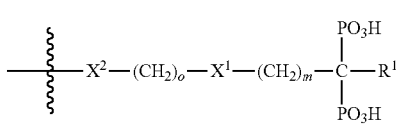

wherein $R^1$ is hydrogen, a hydroxyl group, an alkyl group, an alkylene group, an amine group, a thiol group, or an aryl group;
$X^1$ and $X^2$ are, independently, O, S, or $NR^3$, wherein $R^3$ is hydrogen, an alkyl group, an aryl group, or a cycloalkyl group; and
m and o are, independently, from 1 to 8.

8. The compound of claim 7, wherein $R^1$ is hydrogen, $X^1$ and $X^2$ are S, m is 1, and o is 3.

9. The compound of claim 1, wherein the bisphosphonate-containing group comprises etidronic acid, clodronic acid, tiludronic acid, pamidronic acid, neridronic acid, olpadronic acid, alendronic acid, ibandronic acid, zolendronic acid, or risedronic acid.

10. The compound of claim 1, wherein n is 2, and p is 1.

11. The compound of claim 1, wherein one amino proton present in the mammalian parathyroid hormone is substituted with a group having the formula I.

12. The compound of claim 1, wherein the mammalian parathyroid hormone is SEQ ID NO: 2, and wherein one amino proton of $Ser^1$, $Lys^{13}$, $Lys^{26}$, $Lys^{27}$, or any combination thereof of the mammalian parathyroid hormone is substituted with a group having the formula I.

13. The compound of claim 1, wherein the fragment of mammalian parathyroid hormone is SEQ ID NO: 1, and wherein one amino proton of $Ser^1$, $Lys^{13}Lys^{26}$, $Lys^{27}$ or any combination thereof of the fragment of mammalian parathyroid hormone is substituted with a group having the formula I.

14. The compound of claim 1, wherein at least two, three or four different amino protons present in the mammalian parathyroid hormone are substituted with a group having the formula I.

15. A pharmaceutical composition comprising the compound of claim 1 and a pharmaceutically acceptable carrier.

16. A method of treating loss of bone mass in a subject comprising administering the compound of claim 1 to the subject having a condition that causes loss of bone mass.

* * * * *